United States Patent [19]

Becker et al.

[11] Patent Number: 4,585,881
[45] Date of Patent: Apr. 29, 1986

[54] 2,5-DIHYDRO-5-ARYLIMINOPYRROLE DERIVATIVES AND THEIR PREPARATION

[75] Inventors: Rainer Becker, Bad Durkheim; Bruno Wuerzer, Otterstadt, both of Fed. Rep. of Germany

[73] Assignee: BASF Aktiengesellschaft, Fed. Rep. of Germany

[21] Appl. No.: 584,864

[22] Filed: Feb. 29, 1984

[30] Foreign Application Priority Data

Mar. 9, 1983 [DE] Fed. Rep. of Germany ....... 3308297

[51] Int. Cl.$^4$ ........................................... C07D 207/436
[52] U.S. Cl. ..................................... 548/544; 544/239
[58] Field of Search ......................................... 548/544

[56] References Cited

U.S. PATENT DOCUMENTS 3,072,673  1/1963  de Benneville et al. ............. 260/313
4,064,140  12/1977  Adam ................................. 548/544

OTHER PUBLICATIONS

Maki et al., Chem. Pharm. Bull., 19, (1971), pp. 1635–1640.
Borsche et al., Ann., (1904), 331, pp. 298–318.
Hollins, "Synthesis of Nitrogen Ring Compounds" p. 89 (1924).

*Primary Examiner*—Glennon H. Hollrah
*Assistant Examiner*—D. B. Springer
*Attorney, Agent, or Firm*—Keil & Weinkauf

[57] ABSTRACT

2,5-Dihydro-5-aryliminopyrrole derivatives of the formula

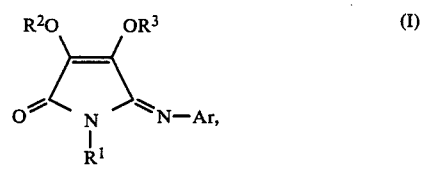

where $R^1$ is hydrogen or alkyl, $R^2$ and $R^3$ are each alkyl, and Ar is unsubstituted or substituted aryl, are used for controlling undesirable plant growth.

5 Claims, No Drawings

2,5-DIHYDRO-5-ARYLIMINOPYRROLE DERIVATIVES AND THEIR PREPARATION

The present invention relates to 2,5-dihydro-5-aryliminopyrrole derivatives, a process for their preparation, and herbicides which contain these compounds as active ingredients.

We have found that 2,5-dihydro-5-aryliminopyrrole derivatives of the formula

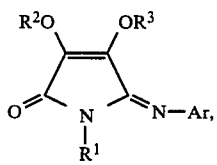

where $R^1$ is hydrogen or $C_1$-$C_4$-alkyl, $R^2$ and $R^3$ are each $C_1$-$C_4$-alkyl, and Ar is unsubstituted or substituted aryl, possess herbicidal activity.

In the general formula I, $R^1$, $R^2$ and $R^3$ independently of one another are each a straight-chain or branched $C_1$-$C_4$-alkyl radical, eg. methyl, ethyl, i-propyl, n-butyl, sec.-butyl or i-butyl, preferably methyl, ethyl or i-propyl.

Ar is unsubstituted or substituted aryl, eg. phenyl or naphthyl, preferably phenyl. The radicals can carry not more than three identical or different substituents selected from the group consisting of cyano, halogen, $C_1$-$C_4$-alkyl, $C_1$-$C_4$-alkoxy, $C_1$-$C_4$-haloalkyl and $C_1$-$C_4$-haloalkoxy. Examples of unsubstituted or substituted radicals Ar are phenyl, α-naphthyl, β-naphthyl, fluorophenyl, difluorophenyl, chlorophenyl, dichlorophenyl, bromophenyl, dibromophenyl, trichlorophenyl, trifluoromethylphenyl, difluoromethylphenyl, methoxyphenyl, ethoxyphenyl, i-propoxyphenyl, tolyl, difluoromethoxyphenyl, trifluoromethoxyphenyl, tetrafluoroethoxyphenyl and cyanophenyl. These phenyl radicals carry the substituents in the 2-, 3-, 4-, 2,4-, 3,4-, 3,5- or 2,4,6-positions.

Preferred 2,5-dihydro-5-aryliminopyrrole derivatives are compounds of the formula I where $R^1$ is hydrogen or methyl, $R^2$ and $R^3$ are each methyl, and Ar is phenyl which is unsubstituted or monosubstituted or disubstituted by halogen, $C_1$-$C_4$-alkyl, $C_1$-$C_4$-haloalkyl or $C_1$-$C_4$-haloalkoxy. Preferred halogen substituents for the phenyl radicals are fluorine and chlorine.

We have furthermore found that 2,5-dihydro-5-aryliminopyrrole derivatives of the formula

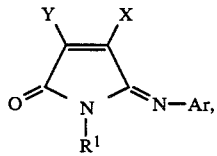

where $R^1$ is hydrogen, X is alkyl, alkoxy, dialkylamino or unsubstituted or substituted phenyl, Y is hydrogen, halogen or alkoxy and Ar is unsubstituted or substituted aryl, are obtained if a pyridazinone of the formula

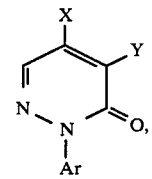

where X, Y and Ar have the above meanings, is converted with a base, in the presence of an inert solvent and at from 0° to 100° C., to a 2,5-dihydro-5-aryliminopyrrole derivative of the formula Ia.

A similar reaction in which a pyrazinone structure is converted to an iminopyrrole with cleavage of the N—N bond has not been described in the literature to date. All ring contraction reactions involving pyridazinone which have been described to date take place with retention of the N—N bond, and give pyrazole derivatives (German Published Applications DAS 1,229,095 and DAS 1,133,383; Chem. Pharm. Bull. 19 (1971), 1635; ibid. 20 (1972), 747; ibid. 22 (1974), 229 and Tetrahedron Lett. 19 (1971), 1507. The novel reaction for the preparation of the 2,5-dihydro-5-aryliminopyrrole derivatives of the formula Ia, which takes place under mild conditions and gives very good yields, must therefore be regarded as very surprising.

The ring contraction of the pyridazinone of the formula IIa to give a 2,5-dihydropyrrol-2-one takes place in the presence of a base, examples of suitable bases being alkali metal hydroxides, such as sodium hydroxide or potassium hydroxide, alkali metal alcoholates, such as sodium methylate, potassium methylate or sodium ethylate, and sodium hydride.

The amount of base is from 0.5 to 1.5, preferably from 1.0 to 1.1, moles per mole of the pyridazinone of the formula II.

Particularly suitable inert solvents are dipolar, aprotic solvents, such as dimethyl sulfoxide, dimethylformamide, dimethylacetamide or sulfolane.

Alkylation of 2,5-dihydro-5-arylimino-3,4-dialkoxypyrrol-2-ones which are unsubstituted in the 1-position can be carried out in a conventional manner, using a conventional alkylating agent, such as an alkyl halide, an alkyl sulfate or an alkyl tosylate.

The reaction is advantageously carried out as follows: the pyridazinone of the formula IIa in an inert solvent is initially taken, and the base is added while stirring. The reaction is carried out at from 0° to 100° C., preferably from 20° to 50° C. The time required depends in particular on the solvent and the base, and is about 1-50 hours.

The reaction mixture is worked up by stirring it into water and rendering the mixture neutral. The end products of the formula Ia where $R^1$ is hydrogen can then be filtered off under suction or extracted. To prepare the alkylated products of the formula Ia where $R^1$ is $C_1$-$C_4$-alkyl, an alkylating agent is added to the reaction mixture when the rearrangement reaction is complete, but before the mixture is stirred into water. After a reaction time of a further 1 to 20 hours at from 0° to 100° C., working up can be carried out as described above.

In formula Ia, X is $C_1$-$C_4$-alkyl, $C_1$-$C_{10}$-alkoxy, preferably $C_1$-$C_4$-alkoxy, dialkylamino where alkyl is of 1 to 10 carbon atoms, preferably of 1 to 4 carbon atoms, and phenyl which is unsubstituted or substituted by halogen, $C_1$-$C_4$-alkyl, $C_1$-$C_4$-alkoxy or $C_1$-$C_4$-haloalkyl, Y is hydrogen, halogen, preferably fluorine, chlorine or bromine, or $C_1$-$C_{10}$-alkoxy, preferably $C_1$-$C_4$-alkoxy, and Ar is a phenyl or naphthyl radical which can be substituted by halogen, $C_1$-$C_4$-alkyl, $C_1$-$C_4$-alkoxy or $C_1$-$C_4$-haloalkyl.

Examples of the substituents $R^1$ and Ar are the radicals stated for the corresponding substituents in formula I. X is, for example, methyl, ethyl, i-propyl, n-butyl, sec.-butyl, i-butyl, methoxy, ethoxy, n-propoxy, i-butoxy, sec.-butoxy, dimethylamino, diethylamino, di-n-butylamino, phenyl, fluorophenyl, difluorophenyl, chlorophenyl, dichlorophenyl, bromophenyl, dibromophenyl, trichlorophenyl, trifluoromethylphenyl, difluoromethylphenyl, methoxyphenyl, ethoxyphenyl, i-propoxyphenyl or tolyl. Y is, for example, hydrogen, fluorine, chlorine, bromine, methoxy, ethoxy, i-propoxy or n-butoxy.

The Examples which follow illustrate the preparation of the 2,5-dihydro-5-aryliminopyrrole derivatives of the formula I or Ia. In the Examples, parts by weight bear the same relation to parts by volume as that of the kilogram to the liter.

EXAMPLE 1

12 parts by weight of 2-phenyl-4,5-dimethoxypyridazin-3-one were suspended in 150 parts by volume of dimethyl sulfoxide, and 9 parts by weight of a 30% strength solution of sodium methylate in methanol were added dropwise. The mixture was stirred for 20 hours at room temperature, after which it was stirred into 1 liter of ice water and rendered neutral by adding concentrated hydrochloric acid, and the product was filtered off under suction. 11.4 parts by weight of 2,5-dihydro-3,4-dimethoxy-5-phenyliminopyrrol-2-one of melting point 141°–143° C. were obtained (compound No.1).

EXAMPLE 2

30.1 parts by weight of 2-(3,4-dichlorophenyl)-4,5-dimethoxypyridazin-3-one were suspended in 200 parts by volume of dimethyl sulfoxide, and 18 parts by weight of a 30% strength solution of sodium methylate in methanol were added dropwise at room temperature. The mixture was stirred for 20 hours, after which 14.2 parts by weight of methyl iodide were added dropwise, stirring was continued for several hours, the mixture was then poured into 1 liter of ice water, and the resulting precipitate was filtered off under suction. 29.4 parts by weight of 1-methyl-2,5-dihydro-3,4-dimethoxy-5-(3,4-dichlorophenylimino)-pyrrol-2-one of melting point 111°–113° C. were obtained (compound No.53).

EXAMPLE 3

12.4 parts by weight of 2,5-diphenylpyridazin-3-one were suspended in 100 parts by volume of dimethyl sulfoxide, and 9 parts by weight of a 30% strength solution of sodium methylate in methanol were added dropwise. The mixture was stirred for 20 hours, after which it was poured into 500 parts by weight of ice water and rendered neutral with hydrochloric acid, and the precipitated product was filtered off under suction, dried and then purified by introducing it over a silica gel column (mobile phase: methylene chloride). 8.7 parts by weight of 2,5-dihydro-4-phenyl-5-phenyliminopyrrol-2-one of melting point 180°–183° C. were obtained (compound No.62).

EXAMPLE 4

26 percent by weight of 2-phenyl-4-chloro-5-dimethylaminopyridazin-3-one in 200 ml of dimethyl sulfoxide were initially taken, and 18 parts by weight of a 30% strength solution of sodium methylate in methanol were added dropwise. The mixture was stirred for 20 hours at room temperature, after which it was stirred into 500 ml of ice water and rendered neutral with hydrochloric acid, and the resulting product was filtered off under suction. 11.4 parts by weight of 2,5-dihydro-3-chloro-4-dimethylamino-5-phenyliminopyrrol-2-one of melting point 135°–138° C. were obtained (compound No.68).

EXAMPLE 5

18 g of a 30% strength solution of sodium methylate in methanol were introduced into 150 ml of dimethyl sulfoxide, and the mixture was freed from methanol at 70° C. in a rotary evaporator. The resulting suspension was added, a little at a time, to a suspension of 23.7 parts by weight of 2-phenyl-4-chloro-5-methoxypyridazin-3-one in 150 parts by volume of dimethyl sulfoxide. The mixture was stirred for several hours at room temperature, after which it was stirred into 500 parts by weight of ice water and rendered neutral with hydrochloric acid. 19.2 parts by weight of 2,5-dihydro-3-chloro-4-methoxy-5-phenyliminopyrrol-2-one of melting point 179°–180° C. (from toluene) were obtained (compound No.70).

The compounds below, of the formula Ia or I, can be prepared by a similar route.

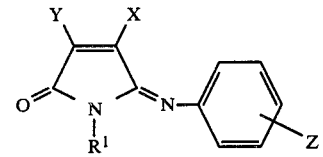

| Compound no. | $R^1$ | Y | X | Z | M.p. [°C.] |
| --- | --- | --- | --- | --- | --- |
| 1 | H | $OCH_3$ | $OCH_3$ | H | 141–143 |
| 2 | H | $OCH_3$ | $OCH_3$ | 3-$CH_3$ | 109–110 |
| 3 | H | $OCH_3$ | $OCH_3$ | 3-$OCF_2CHF_2$ | 110–111 |
| 4 | H | $OCH_3$ | $OCH_3$ | 3-$CF_3$ | 107–110 |
| 5 | H | $OCH_3$ | $OCH_3$ | 3-Br | 108–110 |
| 6 | H | $OCH_3$ | $OCH_3$ | 3-CN | 140–143 |
| 7 | H | $OCH_3$ | $OCH_3$ | 3-$CHF_2$ | 100–103 |
| 8 | H | $OCH_3$ | $OCH_3$ | 3-$OCHF_2$ | |
| 9 | H | $OCH_3$ | $OCH_3$ | 3-$OCF_2CHFCl$ | |
| 10 | H | $OCH_3$ | $OCH_3$ | 3-Cl | |
| 11 | H | $OCH_3$ | $OCH_3$ | 3-F | |
| 12 | H | $OCH_3$ | $OCH_3$ | 3-$OCH_3$ | 103–105 |
| 13 | H | $OCH_3$ | $OCH_3$ | 2-F | 146–148 |
| 14 | H | $OCH_3$ | $OCH_3$ | 2-$OCHF_2$ | 114–116 |
| 15 | H | $OCH_3$ | $OCH_3$ | 2-$CH_3$ | |
| 16 | H | $OCH_3$ | $OCH_3$ | 2-$OCH_3$ | |
| 17 | H | $OCH_3$ | $OCH_3$ | 4-F | |
| 18 | H | $OCH_3$ | $OCH_3$ | 4-Cl | |
| 19 | H | $OCH_3$ | $OCH_3$ | 4-$CH_3$ | |
| 20 | H | $OCH_3$ | $OCH_3$ | 4-$OCH_3$ | |
| 21 | H | $OCH_3$ | $OCH_3$ | 3,4-$Cl_2$ | 133–135 |
| 22 | H | $OCH_3$ | $OCH_3$ | 3,5-$Cl_2$ | 156–158 |
| 23 | H | $OCH_3$ | $OCH_3$ | 2,4-$Cl_2$ | |
| 24 | H | $OCH_3$ | $OCH_3$ | 2,6-$Cl_2$ | |
| 25 | H | $OCH_3$ | $OCH_3$ | 2,4,6-$Cl_3$ | |
| 26 | H | $OCH_3$ | $OCH_3$ | 2,4-$F_2$ | 128–129 |
| 27 | H | $OCH_3$ | $OCH_3$ | 3,4-$F_2$ | 141–143 |
| 28 | H | $OCH_3$ | $OCH_3$ | 3-Cl, 4-F | 151–153 |
| 29 | H | $OCH_3$ | $OCH_3$ | 3-$CF_3$, 4-F | 150–153 |
| 30 | H | $OCH_3$ | $OCH_3$ | 3-Cl, 4-$OCHF_2$ | 118–120 |
| 31 | H | $OCH_3$ | $OCH_3$ | 3,5-$(CH_3)_2$ | |
| 32 | H | $OCH_3$ | $OCH_3$ | 3-$C_2H_5$ | |

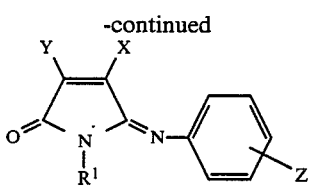

| Compound no. | R¹ | Y | X | Z | M.p. [°C.] |
|---|---|---|---|---|---|
| 33 | H | OCH₃ | OCH₃ | 3-CH₃, 4-F | 133–136 |
| 34 | H | OCH₃ | OCH₃ | 4-CH(CH₃)₂ | |
| 35 | H | OC₂H₅ | OC₂H₅ | H | |
| 36 | CH₃ | OCH₃ | OCH₃ | H | 57–58 |
| 37 | CH₃ | OCH₃ | OCH₃ | 3-CF₃ | |
| 38 | CH₃ | OCH₃ | OCH₃ | 3-Cl | |
| 39 | CH₃ | OCH₃ | OCH₃ | 3-F | |
| 40 | CH₃ | OCH₃ | OCH₃ | 3-Br | 99–101 |
| 41 | CH₃ | OCH₃ | OCH₃ | 3-CN | |
| 42 | CH₃ | OCH₃ | OCH₃ | 3-CHF₂ | 77–79 |
| 43 | CH₃ | OCH₃ | OCH₃ | 3-OCH₃ | |
| 44 | CH₃ | OCH₃ | OCH₃ | 3-OCHF₂ | |
| 45 | CH₃ | OCH₃ | OCH₃ | 3-OCF₂CHF₂ | |
| 46 | CH₃ | OCH₃ | OCH₃ | 2-F | |
| 47 | CH₃ | OCH₃ | OCH₃ | 2-OCHF₂ | |
| 48 | CH₃ | OCH₃ | OCH₃ | 2-CH₃ | |
| 49 | CH₃ | OCH₃ | OCH₃ | 4-F | |
| 50 | CH₃ | OCH₃ | OCH₃ | 4-Cl | |
| 51 | CH₃ | OCH₃ | OCH₃ | 4-OCH₃ | |
| 52 | CH₃ | OCH₃ | OCH₃ | 4-CH₃ | |
| 53 | CH₃ | OCH₃ | OCH₃ | 3,4-Cl | 111–113 |
| 54 | CH₃ | OCH₃ | OCH₃ | 3,5-Cl₂ | 100–102 |
| 55 | CH₃ | OCH₃ | OCH₃ | 2,4-Cl₂ | |
| 56 | CJ₃ | OCH₃ | OCH₃ | 2,4-F₂ | |
| 57 | CH₃ | OCH₃ | OCH₃ | 3,4-F₂ | 101–103 |
| 58 | CH₃ | OCH₃ | OCH₃ | 3,5-(CH₃)₂ | |
| 59 | i-C₃H₇ | OCH₃ | OCH₃ | H | |
| 60 | CH₃ | OC₂H₅ | OC₂H₅ | H | |
| 61 | C₂H₅ | OCH₃ | OCH₃ | H | |
| 62 | H | H | C₆H₅ | H | 180–183 |
| 63 | H | Cl | C₆H₅ | H | |
| 64 | H | H | CH₃ | H | |
| 65 | H | Cl | CH₃ | H | |
| 66 | H | Br | CH₃ | H | |
| 67 | H | H | OCH₃ | H | 156–159 |
| 68 | H | Cl | N(CH₃)₂ | H | 135–138 |
| 69 | H | Cl | N(C₂H₅)₂ | H | |
| 70 | H | Cl | OCH₃ | H | 179–180 |
| 71 | H | F | OCH₃ | H | |
| 72 | H | Br | OCH₃ | H | |

The 2,5-dihydro-5-arylimino-pyrrole derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 46 is mixed with 10 parts by weight of N-methyl-alpha-pyrrolidone. A mixture is obtained which is suitable for application in the form of very fine drops.

II. 10 parts by weight of compound no. 3 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 1 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 36 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 22 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 33 is intimately mixed with 95 parts by weight of particulate kaolin. A dust is obtained containing 5% by weight of the active ingredient.

VII. 30 parts by weight of compound no. 27 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 57 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well when they are applied postemergence, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.05 to 5 kg/ha and more, but is preferably from 0.25 to 3.0 kg/ha.

The herbicidal action of 2,5-dihydro-5-arylimino-pyrrole derivatives of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. No covers were placed on the pots in this treatment method. The application rates for postemergence treatment were 0.5 and 3.0 kg of active ingredient per hectare.

The pots were set up in the greenhouse—species from warmer areas at from 20° to 35° C., and species from moderate climates at 20° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Amaranthus spp., Avena sativa, Cassia tora, Centaurea cyanus, Chenopodium album, Galium aparine, Gossypium hirsutum, Ipomoea spp., Mercurialis annua, Sinapis alba, and Zea mays.

On preemergence application, for example compounds nos. 1 and 36 had a considerable herbicidal action, as did compound no. 3, which was also selective in oats.

On postemergence application, for example compounds nos. 3, 7, 22, 27, 33, 36, 46 and 57, applied at a rate of 3 kg/ha, had a herbicidal action on broadleaved unwanted plants. Compound no. 1 had a selective action on weeds at a rate of, for example, 0.5 kg/ha, or only caused slight damage to cotton and Indian corn.

In view of the tolerance of the compounds according to the invention and the numerous application methods possible, they may be used in a large number of crops for removing unwanted wild grasses or grassy crop plants growing where they are not desired. The following crops may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | |
| *Brassica napus* var. *rapa* | turnips |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica (Coffea canephora, Coffea liberica)* | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* | cotton |

-continued

| Botanical name | Common name |
| --- | --- |
| (Gossypium arboreum | |
| Gossypium herbaceum | |
| Gossypium vitifolium) | |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum | tobacco |
| (N. rustica) | |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum | parsley |
| spp. tuberosum | |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the 2,5-dihydro-5-arylimino-pyrrole derivatives of the formula I, or agents containing them, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, cyclohexane-1,3-dione derivatives, etc., and others, e.g., 3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4-(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N,N-di-n-propyl-2,6-dinitro-3-amino-4-trifluoromethylaniline
N,N-di-n-propyl-2,6-dinitro-4-methylaniline
N,N-di-n-propyl-2,6-dinitro-4-methylsulfonylaniline
N,N-di-n-propyl-2,6-dinitro-4-aminosulfonylaniline
N,N-di-β-chloroethyl-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate 3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-ethylhexahydro-1-H-azepine-1-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
alpha,alpha-dichloropropionic acid, sodium salt
alpha,alpha-dichlorobutyric acid, sodium salt
alpha,alpha,beta,beta-tetrafluoropropionic acid, sodium salt
alpha-methyl-alpha,beta-dichloropropionic acid, sodium salt
methyl alpha-chloro-beta-(4-chlorophenyl)-propionate
methyl alpha,beta-dichloro-beta-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-(3,4-dichlorophenyl)-amino)-propionate methyl 2-(N-benzoyl-3-chloro-4-fluorophenylamino)-propionate isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-isopropyl-5-bromo-6-methyluracil
3-sec.butyl-5-bromo-6-methyluracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(1-methylpropyn-2-yl)-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(pyrazolyl-methyl)-2-chloroacetanilide
2,6-dimethyl-N-(pyrazolyl-methyl)-2-chloroacetanilide
2,6-dimethyl-N-(4-methylpyrazolyl-methyl)-2-chloroacetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-(n-butoxymethyl)-2-chloroacetanilide
2,6-diethyl-N-ethoxycarbonylmethyl-2-chloroacetanilide
2,3-dimethyl-N-isopropyl-2-chloroacetanilide
2,6-diethyl-N-(2-n-propoxyethyl)-2-chloroacetanilide
alpha-(2-methyl-4-chlorophenoxy)-N-methoxyacetamide
2-(alpha-naphthoxy)-N,N-diethylpropionamide
2,2-diphenyl-N,N-dimethylacetamide
alpha-(3,4,5-tribromopyrazol-1-yl)-N,N-dimethylpropionamide
N-(1,1-dimethylprop-2-ynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid hexamethylene imide
2,6-dichlorothiobenzamide
2,6-dichlorobenzonitrile
3,5-dibromo-4-hydroxybenzonitrile (salts)
3,5-diiodo-4-hydroxybenzonitrile (salts)

3,5-dibromo-4-hydroxy-O-2,4-dinitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
3-(4-bromophenyl)-3,4,5,9,10-pentaazatetracyclo-[5,4,1,O$^{2,6}$,O$^{8,11}$]-dodeca-3,9-diene
2-ethoxy-2,3-dihydro-3,3-dimethyl-5-benzofuranylmethane sulfonate
2-methyl-4,6-dinitrophenol (salts, esters)
3-(4-chlorophenyl)-3,4,5,9,10-pentaazatetracyclo-[5,4,1,O$^{2,6}$,O$^{8,1}$]-dodeca-3,9-diene
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(alpha,alpha-dimethylbenzyl)-3-(4-methylphenyl)-urea
1-phenyl-3-(2-methylcyclohexyl)-urea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-3-methyl-3-n-butylurea
1-(4-isopropylphenyl)-3,3-dimethylurea
1-(3-trifluoromethylphenyl)-3,3-dimethylurea
1-(alpha,alpha-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2,4-dichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl alpha-naphthoxyacetate
2-(2,4-dichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate trithiobutylphosphite
O,O-diisopropyl-5-(2-benzosulfonylaminoethyl)-phosphorodithioate
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
3-tert.-butylamino-4-methoxycarbonyl-5-methyl-pyrazole
N-benzyl-N-isopropyl-trimethylacetamide
methyl 2-[4-(4'-chlorophenoxymethyl)-phenoxy]-propionate ethyl 2-[4-(5'-bromopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxyamino)-butylidene]-5-(2-ethylthiopropyl)-3-hydroxy-cyclohex-2-en-1-one (salts)
2-[1-(N-ethoxyamino)-butylidene]-5-(2-phenylthiopropyl)-3-hydroxy-cyclohex-2-en-1-one (salts)
ethyl 4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)
4,5-dimethoxy-2-(3-alpha,alpha,beta-trifluoro-beta-bromoethoxyphenyl)-3-(2H)-pyridazinone
2,4-dichloro-3'-[2-(2-ethoxy-ethoxy)-ethoxy]-4'-nitrodiphenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-pyridine
1(-4-[2-(4-methylphenyl)-ethoxy]-phenyl)-3-methyl-3-methoxyurea
2,6-dimethyl-N-(pyrazol-methylenoxymethyl)-2-chloroacetanilide
2-methyl-6-ethyl-N-(pyrazolyl-methylenoxymethyl)-2-chloroacetanilide
alpha-2,4-dichlorophenoxy-propionic acid)-(3-methoxycarbonylamino)-anilide
1-(alpha-2-bromo-4-chlorophenoxypropionic acid)-3-(O-methylcarbamoyl)-anilide
2-methyl-6-ethyl-N-(pyrazolyl-ethylenoxymethyl)-2-chloroacetanilide
2-(3-trifluoromethylphenyl)-4H-3,1-benzoxazin-4-one
2-(3-pentafluoroethoxyphenyl)-4H-3,1-benzoxazin-4-one
2-(3-trifluoromethylthio-phenyl)-4H-3,1-benzoxazin-4-one
2-(3-difluorochloromethoxyphenyl)-4H-3,1-benzoxazin-4-one
5-nitro-2-(3-trifluoromethyl-phenyl)-4H-3,1-benzoxazin-4-one
5-chloro-2-(3-trifluoromethoxyphenyl)-4H-3,1-benzoxazin-4-one
5-chloro-2-(3-alpha,alpha,beta,beta-tetrafluoroethoxyphenyl)-4H-3,1-benzoxazin-4-one
5-fluoro-2-(3-alpha,alpha,beta,beta-tetrafluoroethoxyphenyl)-4H-3,1-benzoxazin-4-one
5-chloro-2-(4-difluorochloromethoxyphenyl)-4H-3,1-benzoxazin-4-one
5-fluoro-2-(4-difluorochloromethoxyphenyl)-4H-3,1-benzoxazin-4-one
5-fluoro-2-phenyl-4H-3,1-benzoxazin-4-one
5-fluoro-2-(3-difluoromethoxyphenyl)-4H-3,1-benzoxazin-4-one
5-chloro-2-phenyl-4H-3,1-benzoxazin-4-one
methyl N-3-chloro-4-isopropylphenyl-thiolcarbamate
6-methyl-3-methoxy-5,6-dihydro-1,2,4,6-thiatriazin-5-one-1,1-dioxide, sodium salt
6-methyl-3-ethoxy-5,6-dihydro-1,2,4,6-thiatriazin-5-one-1,1-dioxide
5-amino-4-chloro-2-phenyl-3(2H)-pyridazinone
5-amino-4-bromo-2-phenyl-3(2H)-pyridazinone
5-methylamino-4-chloro-2-(3-trifluoromethylphenyl)-3(2H)-pyridazinone
5-methylamino-4-chloro-2-(3-alpha,alpha,beta,beta-tetrafluoroethoxyphenyl)-3(2H)-pyridazinone
5-dimethylamino-4-chloro-2-phenyl-3(2H)-pyridazinone 4,5-dimethoxy-2-phenyl-3(2H)-pyridazinone
1-[3'-(2''-chloro-4''-trifluoromethylphenoxy)]-phenyl-4,5-di-methoxy-pyridazin-6-one
1-[4'-(3''-trifluoromethyl-phenoxy)]-phenyl-4,5-dimethoxy-pyridazin-6-one
4,5-dimethoxy-2-(3-alpha,alpha,beta-trifluoro-beta-bromoethoxyphenyl)-3-(2H)-pyridazinone
methyl N-[4-(4'-methoxy-phenoxy)-3-chlorophenyl]-carbamate
methyl N-[4-(4'-difluoromethoxy-phenoxy)-3-chlorphenyl]-thio-carbamate
methyl N-[4-(4'-difluoromethoxy-phenoxy)-phenyl]thio-carbamate
1-[4-(4'-methylphenylpropyl)-phenyl]-3-methyl-3-methoxyurea
1-[3-(4'-chlorophenyl-propyl)-phenyl]-3-methyl-3-methoxyurea
1-[4-(3-phenyl-2-methyl-propyl)-phenyl]-3-methyl-3-methoxyurea
1-[4-(3-(4'-chlorophenyl)-2-methyl-propyl)-phenyl]-3-methyl-3-methoxyurea
1-[4-(3-(4'-methylphenyl)-2-methylpropyl)-phenyl]-3-methyl-3-methoxyurea
2-[1-(N-ethyloxyamino)-butylidene]-5-(4-ethylphenyl)-3-hydroxy-cyclohexen-(2)-one-(1) (salts)
2-[1-(N-ethyloxyamino)-butylidene]-5-(4-fluorophenyl)-3-hydroxy-cyclohexen-(2)-one-(1) (salts)
2-[1-(N-ethyloxyamino)-butylidene]-5-(4-chlorophenyl)-3-hydroxy-cyclohexen-(2)-one-(1) (salts)
methyl 2'-(2,4,6-trichlorophenyl)-hydrazino-2-cyanoacrylate
2-[1-(N-ethyloxamino)-butylidene]-5-(1,3,3-trimethylcyclohexen-1-yl-2)-3-hydroxy-cyclohexen-(2)-one-(1) (Salts)
2-[1-(N-ethyloxamino)-butylidene]-5-(2,4,4-trimethylcyclohexen-1-yl-3)-3-hydroxy-cyclohexen-(2)-one-(1) (salts)
2-[1-(N-3-chloroallyl-oxamino)-butylidene]-5-(1-methyl-cyclohex-1-en-4-yl)-3-hydroxy-cyclohexen-(2)-one-(1) (salts)
3-isobutoxy-5-methyl-4-methoxycarbonyl-pyrazole
5-amino-1-(2,4,6-trichlorophenyl)-4-cyano-pyrazole
5-amino-1-(2,4,6-tribromophenyl)-4-cyano-pyrazole
5-amino-1-(2,4,6-trichlorophenyl)-4-methoxycarbonyl-pyrazole
5-amino-(2,4-dichloro-6-bromophenyl)-4-methoxycarbonyl-pyrazole
5-amino-(2,6-dichloro-4-bromophenyl)-4-methoxycarbonyl-pyrazole
5-chloro-2-(3-trifluoromethyl-phenyl)-4H-3,1-benzoxazin-4-one
5-fluoro-2-(3-trifluoromethyl-phenyl)-4H-3,1-benzoxazin-4-one
2-(3-tetrafluoroethoxyphenyl)-4H-3,1-benzoxazin-4-one
5-chloro-2-(4'-fluorophenyl)-4H-3,1-benzoxazin-4-one
5-fluoro-2-(4'-fluorophenyl)-4H-3,1-benzoxazin-4-one
5-fluoro-2-(3'fluorophenyl)-4H-3,1-benzoxazin-4-one 5-chloro-2-(3'-fluorophenyl)-4H-3,1-benzoxazin-4-one
5-chloro-2-(3'-difluorochlormethylphenyl)-4H-3,1-benzoxazin-4-one
5-fluoro-2-(3'-difluorochlormethylphenyl)-4H-3,1-benzoxazin-4-one
6-methyl-3-methoxy-5-(4'-nitrophenoxy)-6H-1,2,4,6-thiatriazine-1,1-dioxide
6-methyl-3-methoxy-5-(propargyloxy-6H-1,2,4,6-thiatriazine-1,1-dioxide
6-methyl-3-methoxy-5-(2,4-dichlorobenzoxy)-6H-1,2,4,6-thiatriazine-1,1-dioxide
2-(2',4'-dichlorophenoxy)-2-fluoropropionic acid (salts, esters)
butyl 2-[4-(5'-trifluoromethylpyridyl-2-oxy)-phenoxy]-propionate
2-[4-(3'-chloro-5'-trifluoromethylpyridyl-2-oxy)-phenoxy]-propionic acid (salts, esters)
pentyl 2-[4-(6-chloroquinoxalyl-2-oxy)-phenoxy]-propionate
methyl 2-[4-(6-chloroquinoxalyl-2-oxy)-phenoxy]-propionate
2-[4-(6-chlorobenzthiazolyl-2-oxy)-phenoxy]-propionic acid (salts, esters)
2-[4-(6-chlorobenzoxazolyl-2-oxy)-phenoxy]-propionic acid (salts, esters)
1-[5-(3-fluorobenzylthio)-thiadiazolyl-2]-1-methylurea
2-methoxycarbonyl-N-(3,5-dimethylpyrimidinyl-2-aminocarbonyl)-benzole sulfonamide
alpha-(3,5,6-trichloropyrid-2-yl-oxy)-acetic acid (salts, esters)
alpha-(4-amino-3,5-dichloro-6-fluoro-pyrid-2-yl-oxy)-acetic acid (salts, esters)
S-[N-(4-chlorophenyl)-N-isopropyl-carbamoyl-methyl]-O,O-dimethyl-dithiophosphate
ammonium-(3-amino-3-carboxy-propyl)-methylphosphinate (hydroxy)-(methyl)-phosphinyl-L-alpha-aminobutyryl-L-alanyl, sodium salt
4-trifluoromethyl-diphenyl ether
2-(3,5-dichlorophenyl)-2-(2',2',2'-trichloroethyl)-oxirane
2,4-diamino-5-methylthio-6-chloropyrimidine
N-(4-ethylthio-2-trifluoromethyl-phenyl)-methylsulfonamide 3-methoxy-4-methyl-5-(3-methyl-2-butenyloxy)-1,2-di(hydroxymethyl)-benzole
2-(3,5-dimethylphenoxy)-2-(1,2,4-triazolyl-1)-acetic acid-N-tert-butylamide
2-(3,5-dichlorophenoxy)-2-(1,2,4-triazolyl-1)-acetic acid-N-tert-butylamide
3,7-dichloro-8-quinolinecarboxylic acid (salts, esters)
5-(2-chloro-4-trifluoromethyl-phenoxy)-N-(1-methoxycarbonylethoxy)-benzamide
N-[3-(1-ethyl-1-methylpropyl)-isoxazolyl-5]-2,6-dimethoxybenzamide
2'-methoxyethyl-2-[5-(2-chloro-4-trifluoromethyl-phenoxy)-2-nitrophenoxy]-propionate
methyl-6-(4-isopropyl-4-methyl-5-oxo-2-imidazolin-2-yl)-3-methylbenzoate
methyl-6-(4-isopropyl-4-methyl-5-oxo-2-imidozin-2-yl)-4-methylbenzoate
benzyltrimethylammonium chloride
1-[alpha-(4-trifluoromethyl-phenoxy)-phenoxy-propionic acid]-3- -(O-methylcarbamoyl)-anilide
1-dodecyl-cycloheptan-2-one
N-[2-chloro-4-methylsulfonyl-phenyl]-chloromethanesulfonamide
N-[2-bromo-4-ethylsulfonyl-phenyl]-chloromethanesulfonamide
N-[2,3-dichloro-4-(ethylsulfonyl)-phenyl]-chloromethanesulfonamide
2-[1-(N-ethoxyamino)-pyropylidene]-5-(pyrid-3-yl)-3-hydroxy-cyclohex-2-en-1-one (salts)
2,4,5-trichlorophenoxyacetic acid (salts, esters, amides)

It may also be useful to apply the 2,5-dihydro-5-aryliminopyrrole derivatives of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A 2,5-dihydro-5-aryliminopyrrole derivative of the formula

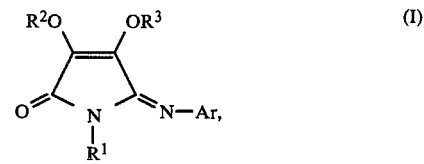

where $R^1$ is hydrogen or $C_1$–$C_4$-alkyl, $R^2$ and $R^3$ are each $C_1$–$C_4$-alkyl, and Ar is unsubstituted phenyl or phenyl substituted by cyano, halogen, $C_1$–$C_4$-alkyl, $C_1$–$C_4$-alkoxy, $C_1$–$C_4$-haloalkyl or $C_1$–$C_4$-haloalkoxy.

2. A 2,5-dihydro-5-aryliminopyrrole derivative of the formula I as defined in claim 1, where Ar is unsubstituted or substituted phenyl.

3. A 2,5-dihydro-5-aryliminopyrrole derivative of the formula I as defined in claim 1, where $R^1$ is hydrogen or methyl, $R^2$ and $R^3$ are each methyl, and Ar is phenyl which is unsubstituted or substituted by halogen, $C_1$–$C_4$-alkyl, $C_1$–$C_4$-haloalkyl or $C_1$–$C_4$-haloalkoxy.

4. A process for the manufacture of 2,5-dihydro-5-aryliminopyrrole derivatives of the formula I as defined in claim 1, wherein a base is added to a pyridazinone of the formula:

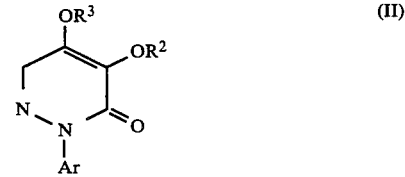

where $R^2$, $R^3$ and Ar have the meanings given in claim 1, in the presence of an inert solvent and at from 0° to 100° C. to convert the pyridazinone (II) to a 2,5-dihydro-5-arylimino-pyrrole derivative of the formula I, $R^1$ denoting hydrogen.

5. A process for the manufacture of 2,5-dihydro-5-aryliminopyrrole derivatives of the formula

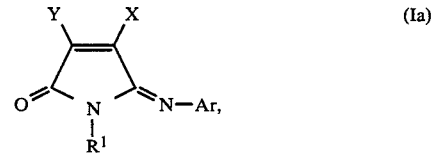

where $R^1$ is hydrogen, X is $C_1$–$C_4$-alkyl, $C_1$–$C_{10}$-alkoxy, dialkylamino, where alkyl is of 1 to 10 carbon atoms or phenyl which is unsubstituted or substituted by halogen, $C_1$-$C_4$-alkyl, $C_1$-$C_4$-alkoxy, or $C_1$-$C_4$-haloalkyl, Y is hydrogen, halogen or $C_1$-$C_{10}$-alkoxy and Ar is unsubstituted phenyl or phenyl substituted by cyano, halogen, $C_1$-$C_4$-alkyl, $C_1$-$C_4$-alkoxy, $C_1$-$C_4$-haloalkyl or $C_1$-$C_4$-haloalkoxy, wherein a base is added to a pyridazinone of the formula

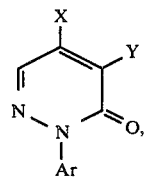
(IIa)

where X, Y and Ar have the above meanings in the presence of an inert solvent and at from 0° to 100° C. to convert the pyridazinone (IIa) to a 2,5-dihydro-5-aryliminopyrrole derivative of the formula Ia.

* * * * *